(12) United States Patent
Heasley

(10) Patent No.: US 7,018,206 B2
(45) Date of Patent: Mar. 28, 2006

(54) RUBBER DAM FRAMES WITH IMPROVED RETRACTION, STABILITY, AND SAFETY CHARACTERISTICS

(76) Inventor: John Heasley, 1614 Dover St., Iowa City, IA (US) 52240

(*) Notice: Subject to any disclaimer, the term of this patent is extended or adjusted under 35 U.S.C. 154(b) by 0 days.

(21) Appl. No.: 10/334,950

(22) Filed: Dec. 31, 2002

(65) Prior Publication Data

US 2004/0126739 A1     Jul. 1, 2004

(51) Int. Cl.
A61C 5/14        (2006.01)
(52) U.S. Cl. ..................................... 433/136
(58) Field of Classification Search ................ 433/136, 433/137, 138, 139, 140
See application file for complete search history.

(56) References Cited

U.S. PATENT DOCUMENTS

| | | | | |
|---|---|---|---|---|
| 296,992 | A | * | 4/1884 | Moffitt ..................... 433/137 |
| 663,507 | A | * | 12/1900 | Meguiar .................... 433/137 |
| 1,292,133 | A | | 1/1919 | Stoughton |
| 3,396,468 | A | | 8/1968 | Dayhoff |
| 3,781,994 | A | | 1/1974 | Hesselgren |
| 4,259,067 | A | | 3/1981 | Nelson |
| 4,261,697 | A | * | 4/1981 | Newitter .................... 433/137 |
| 4,544,357 | A | | 10/1985 | Williams |
| 4,583,946 | A | | 4/1986 | Shanel |
| 4,600,387 | A | | 7/1986 | Ross |
| 4,664,628 | A | | 5/1987 | Totaro |
| 4,721,465 | A | | 1/1988 | Barasz |
| 4,828,491 | A | | 5/1989 | Gray |
| 4,889,490 | A | * | 12/1989 | Jenkinson ................... 433/136 |
| 5,011,409 | A | | 4/1991 | Gray |
| 5,078,604 | A | | 1/1992 | Malmin |
| 5,098,299 | A | | 3/1992 | Fischer |
| 5,199,872 | A | | 4/1993 | Leal |
| 5,340,313 | A | | 8/1994 | Hussin |
| 5,503,556 | A | | 4/1996 | Leonard |
| 5,803,734 | A | | 9/1998 | Knutson |
| 5,931,673 | A | | 8/1999 | Bolbolan |
| 6,048,202 | A | | 4/2000 | Jensen |
| 6,086,370 | A | | 7/2000 | Jensen |
| 6,093,022 | A | | 7/2000 | Swallow |
| 6,135,770 | A | * | 10/2000 | Bembenek et al. .......... 433/88 |

* cited by examiner

Primary Examiner—Melba N. Bumgarner

(57) ABSTRACT

The present invention relates to a rubber dam frame comprised of two vertical side leg members that are connected by a single uninterrupted lower horizontal member and both a left and right upper horizontal member. The frame has a downwardly curved concave nasal deflection element positioned between the left and right upper horizontal members for increasing patient comfort along with a mechanism for attaching and deflecting excess rubber dam material downward to prevent the material from obstructing the nose and the breathing of the patient. The rubber dam membrane is attached to the rubber dam frame through the use of attachment nibs that face outward from the perimeter of the frame and secure the rubber dam membrane to the frame and allow for improved retraction and stability.

22 Claims, 6 Drawing Sheets

RUBBER DAM FRAMES WITH IMPROVED RETRACTION, STABILITY, AND SAFETY CHARACTERISTICS

BACKGROUND OF THE INVENTION

1. Field of the Invention

This invention relates to a dental rubber dam frame and more particularly to a dental rubber dam frame having improved retraction and stability which also allows for increased patient comfort and safety.

2. Background

The rubber dam is an elastic membrane used in dentistry to isolate an intra-oral operative site that is to be worked on by the dentist. It is used at the operative site in order to help the dentist control moisture when the procedure requires a dry environment, prevent the ingestion and aspiration of foreign objects by the patient, and optimize the overall quality of dental treatment during the procedure. The rubber dam is first secured at the site of operation and then stretched over a framework, which is generally exterior to the mouth of the patient. Early designs of rubber dam frames typically have a "U" shaped frame member that is positioned over the patient's face so that the open portion of the "U" faces upward toward the patient's nose. The rubber dam membrane is stretched over the frame and subsequently secured to the frame with projections or nibs spaced at intervals around the periphery of the frame. In theory, the reciprocal stretching of the membrane stabilizes the frame in relation to the patient's oral cavity.

There are a number of shortcomings of standard prior art frames with this "U" shaped design, with one common problem being the potential liability of the open ends, or legs, of the frame poking the patient in the eye during application of the dam or in the course of treatment. One of the early rubber dam frame designs patented, U.S. Pat. No. 682,308 by L. A. Young on Sep. 10, 1901, entitled Rubber Dam Holder, disclosed a frame having the now standard "U" shape. The U-shaped frame satisfied the general requirements of a rubber dam frame and is the basic design still used today. However, the U-shape frame comprised open, unprotected vertical legs, which is believed to have caused injuries to patients' eyes and faces over the course of the 20$^{th}$ Century. Therefore an improved rubber dam frame, which addressed this issue of potential eye damaging accidents, was designed and patented Oct. 22, 1968 by Richard S. McConville, U.S. Pat. No. 3,406,452, entitled Dental Rubber Dam Frame. Although the inventor retained the "U" shaped configuration of the frame one significant feature of this new frame was the addition of ¼ inch round balls or spheres to the ends of the vertical stems or legs of the frame. These large rounded contour balls or spheres, covered the sharp ends of the legs, such that if there was accidental contact with a patient's eye, permanent damage would be avoided and trauma minimized. This improvement was considered useful and this type of frame gained market share in competing with the original design of the '308 frame and is still used in practice by dentists today.

FIG. 4 is an illustration of a "U" shaped frame of the '452 patent design, with a conventional rubber dam stretched over the framework. The figure also illustrates the dentist's inability to achieve a uniform retraction of the rubber dam membrane when using this type of rubber dam frame. As seen in the figure the frame does not contain an upper element and therefore there is a subsequent lack of retraction of the upper lip, with the slumping of the rubber dam adjacent to the upper front teeth. The illustration also shows excess rubber dam material covering the patient's nostrils, which is known to obstruct breathing and cause discomfort to the patient. Further, FIG. 4 depicts a lack of sufficient number of retraction nibs on the lower transverse horizontal member, which subsequently creates an insufficient retraction of the lower lip. The overall resultant effect of the "U" shaped frames is that they give inadequate support to and retraction of both the patient's upper lip and lower lip, due in part because they lack an upper transverse member and because the scarcity of locations where the rubber dam attached to the frames. A further problem exists with the early designs of rubber dam frames in that the recently invented general field isolation rubber dams are known to need even more labial retraction to provide the required stability in the patients mouth.

Other frames have been introduced to the field of dentistry that are circumferential in design, but these have also lacked a retraction mechanism for adequately retracting and distributing the vector forces required for rubber dam retraction. One such circumferential frame, having the characteristics of a rounded square, was known as the Nygaard-Ostby frame. The Nygaard-Ostby frame provides an upper member that is absent in the other frames, however it has extremely large, sharp projections that engage the rubber dam membrane in order to anchor the rubber dam to the frame. One large, sharp projection is allocated to the upper member, and is placed squarely in the center of the frame, where it is most likely to line up with and injure the patient's nasal septum. This frame, with large, sharp projections radiating in all directions is a menacing looking device, which raises questions about the safety and comfort of the patient during use of the device. While this single rubber dam attachment on an upper member may afford some increased retraction of the upper lip, the design provides this at the expense of interfering with and very likely injuring the patient in the process.

Another shortcoming of the frames found in dentistry, whether they are of the "U" shaped variety or the circumferential Nygaard-Ostby design, is that the frames are designed so that any excess stretched rubber dam membrane in the nasal area flaps over the patient's nose, obstructing breathing and often causing the patient to feel claustrophobic. The patient undergoing dental treatment is already in a heightened state of anxiety or stress, and does not need additional stressors added to the experience of the dental treatment. Currently none of the rubber dam frames available for use in dentistry address the problems caused by having excess rubber dam material in the nasal area, which may lead to obstruction of the patient's breathing and further to feelings of smothering or claustrophobia.

To date the field of dentistry lacks rubber dam frames with design features that adequately support the use of general field isolation rubber dams because as stated above, until recently in dentistry there had not been a thorough systematic design and development of general field isolation rubber dams. The development and introduction of new general field isolation rubber dams and newly designed conventional application rubber dams has evolved from an extensive analysis of the vector forces of stretched elastic rubber dam membranes and their interaction with oral anatomical structures. Therefore it follows that a newly designed rubber dam frame is needed to complement and enhance the function of the newly introduced general field isolation and conventional rubber dams. Beyond the benefits of the improved rubber dam frames for the newly introduced rubber dams, the new frames also improve the retraction, stability, safety, and comfort of existing conventional rubber dam applications as well. The need exists for a rubber dam frame capable of overcoming the shortcomings of the current rubber dam frames while providing improved support and retraction for both the new general field isolation rubber dams and the conventional isolation rubber dams. The improved frames would improve rubber dam applications by taking into account the vector forces of the stretched elastic rubber dam membrane and the way in which the forces are used in order to achieve optimal isolation of the operative site. The frames should effectively eliminate all pointed or protruding elements which may accidentally cause eye injury or injury to the face, allow attachment of the rubber dam membrane to the frame in a complete circumferential manner, to increase retraction and support of the patients lips, and increase support, retention, and retraction for the new general field isolation rubber dams by distributing the tensile forces of the stretched membrane, and further manage excess rubber dam membrane to prevent nasal obstruction and discomfort to the patient.

SUMMARY OF THE INVENTION

The present invention relates to a rubber dam frame comprised of two vertical side leg members connected by a single uninterrupted lower horizontal member and both a left and right upper horizontal member. The frame has a downwardly curved concave nasal deflection element positioned between the left and right upper horizontal members for increasing patient comfort along with a mechanism for attaching and deflecting excess rubber dam material downward to prevent the material from obstructing the nose and the breathing of the patient. The rubber dam membrane is attached to the rubber dam frame through the use of attachment nibs that face outward from the perimeter of the frame to secure the rubber dam membrane to the frame and allow for improved retraction and stability. These and other objects of the present invention will become apparent to those skilled in the art upon reference to the following specification, drawings, and claims.

DETAILED DESCRIPTION OF THE INVENTION

Figure 1:
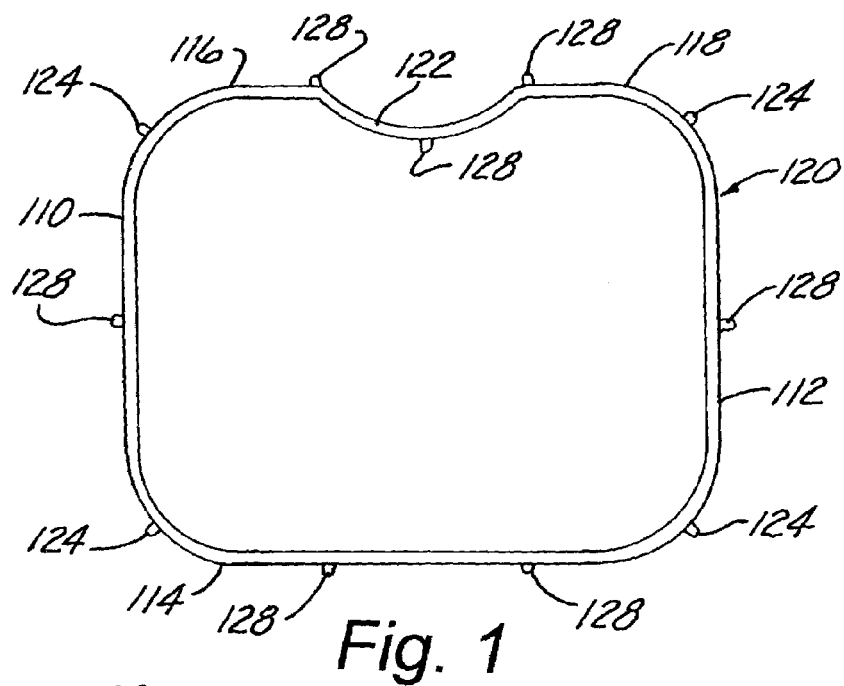
FIG. 1 is a front view of an improved rubber dam frame.
Figure 2:
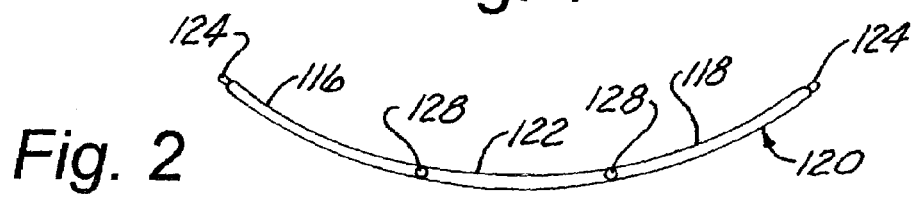
FIG. 2 is a top view of the improved rubber dam frame.
Figure 3:
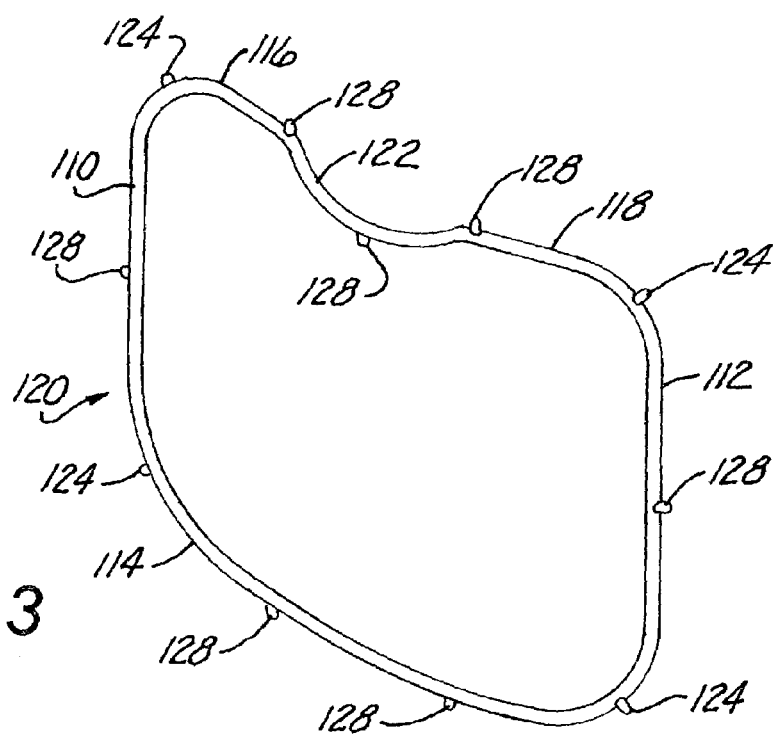
FIG. 3 is an isometric view of the improved rubber dam frame.
Figure 4:
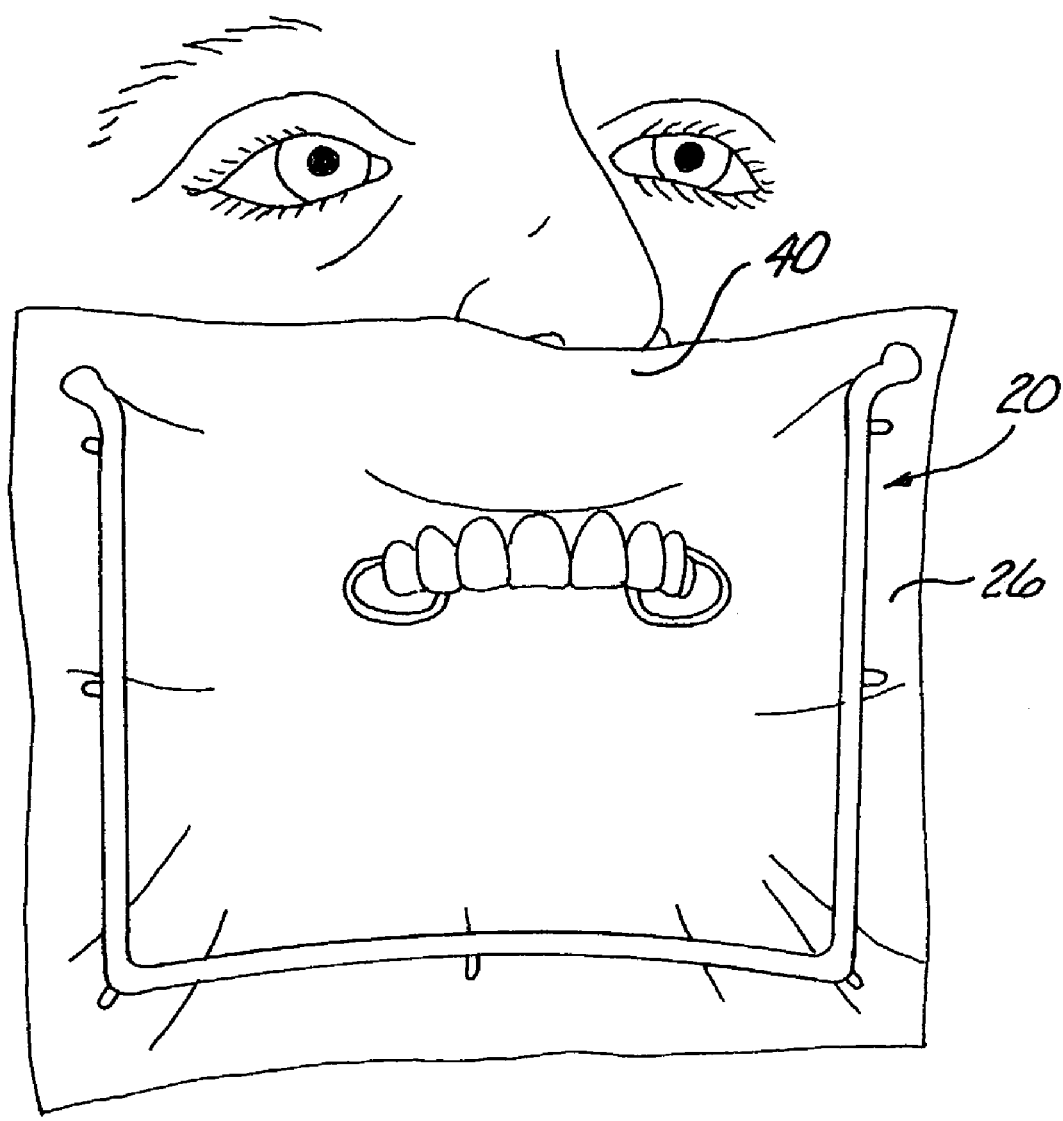
FIG. 4 is an illustration of an early designed "U" shaped rubber dam frame.

FIGS. 1, 2, and 3 illustrate the front view, top view, and isometric view, respectively, of an improved rubber dam frame 120. FIGS. 1 and 3 show vertical side legs 110 and 112, a lower horizontal member 114, a left and right upper horizontal members 116 and 118, and an inwardly curved nasal deflection element 122 of the frame 120. Distributed around the periphery of the frame 120 are small retentive nib projections 124 and 128 positioned on the outside of the frame 120 where a rubber dam membrane 126 is stretched over and attaches to the frame 120 (see FIG. 5). There is a single outwardly facing corner nib projection 124 positioned on each of the four rounded corners. The two vertical side legs 110 and 112 each have an outwardly facing side leg nib projection 128 located at a midpoint of each leg 110 and 112. The left and right upper horizontal members 116 and 118 also have single outwardly facing nib projections 128 located at the point where the nasal deflection element 122 joins with the two upper horizontal members 116 and 118. The lower horizontal element 114 has two outwardly facing attachment nibs 128 each spaced ⅓ of the distance across the lower horizontal element 114. Positioned at the midpoint of the inwardly facing curvature of the nasal deflection element 122 is a single attachment nib 128 facing inward at the height of curvature of the nasal deflection element 122. FIG. 2 shows the arc of curvature of the frame 120 from left to right, which is roughly designed to parallel the curvature of a patient's face. Also seen in FIG. 2 are two of the corner nibs 124, and also the two attachment nibs 128 located on the left and right upper horizontal members 116 and 118. The nasal deflection element 122 is located in the middle between the left and right upper horizontal members 116 and 118.

Figure 5:
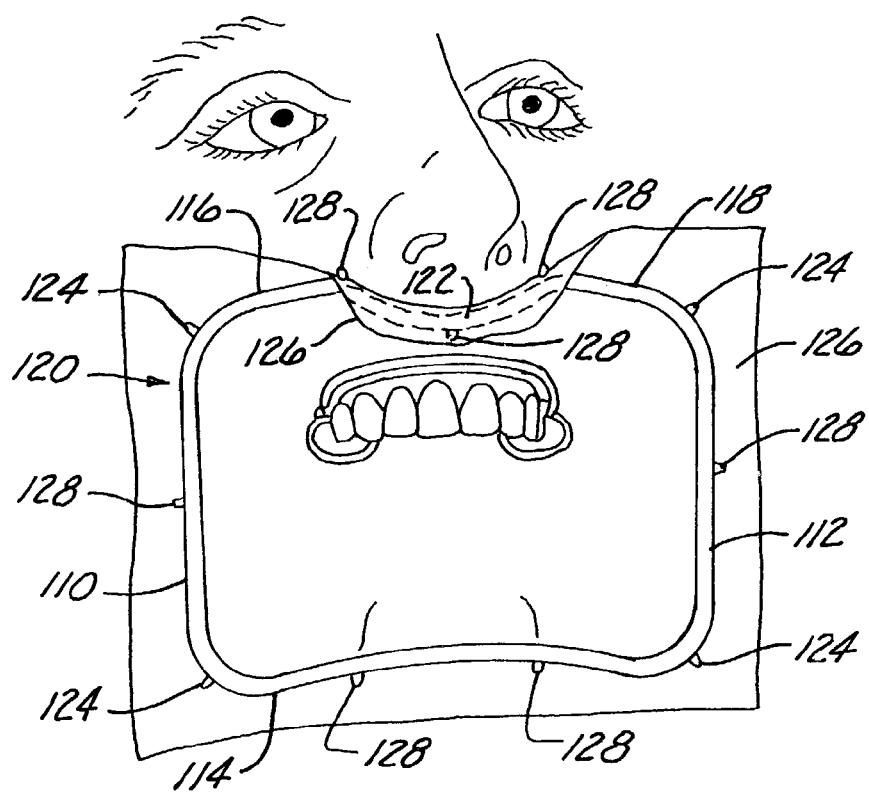
FIG. 5 is an illustration of the improved rubber dam frame as used with a rubber dam membrane.
Figure 6:
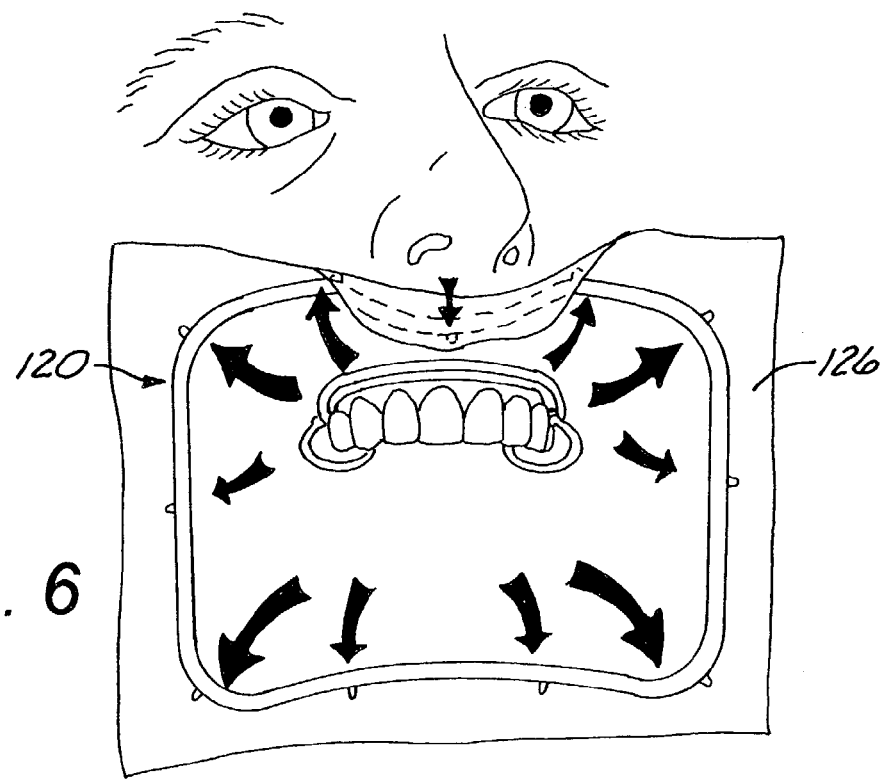
FIG. 6 is an illustration of the improved rubber dam frame with the rubber dam membrane stretched over the frame, with arrows showing the direction and magnitude of vector tensile forces of the stretched rubber dam membrane.

FIG. 5 is a drawing of the preferred embodiment of the improved frame 120, showing the general field isolation rubber dam 126 stretched over the frame 120 with the upper horizontal members 116 and 118 providing improved retraction of the patient's upper lip (not shown), and also showing excess rubber dam material 126 folded downward and secured against the nasal deflection element 122 by the inwardly facing attachment nib 128. FIG. 6 shows the same embodiment as FIG. 5, but includes arrows superimposed over the illustration, demonstrating the direction and magnitude of internal tensile forces that the improved rubber dam frame 120 generates in order to more adequately distribute and balance these tensile forces to increase stability of the dam membrane 126 and improve retraction of the patient's upper and lower lips (not shown). This pattern of distribution of forces coincidentally stabilizes the new general field isolation rubber dams 126 and also stabilizes newly designed conventional rubber dam applications, as well as improving retraction and stability of prior art conventional rubbers dams 126.

Figure 7:
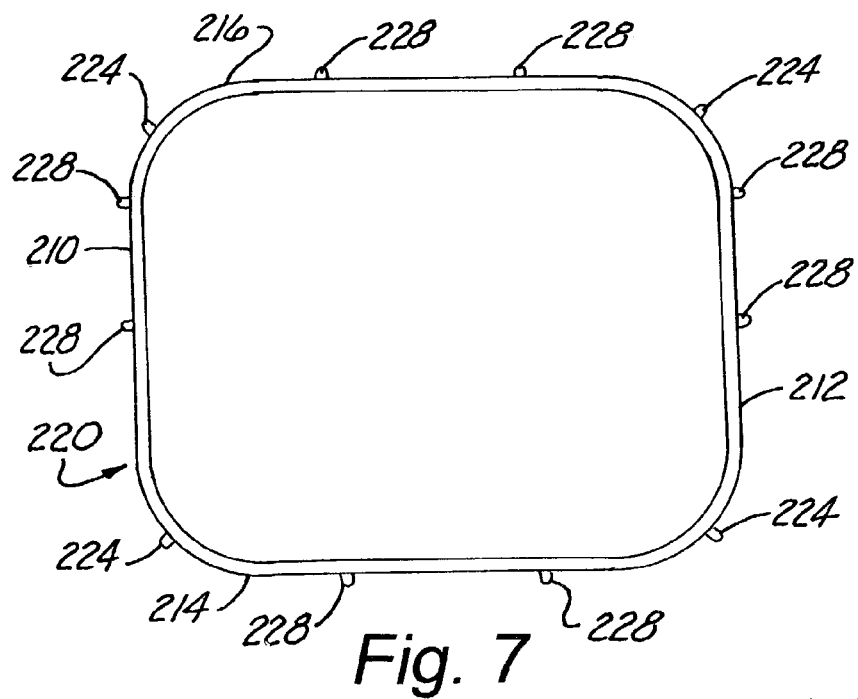
FIG. 7 is a front view of an alternative embodiment of an improved rubber dam frame.
Figure 8:
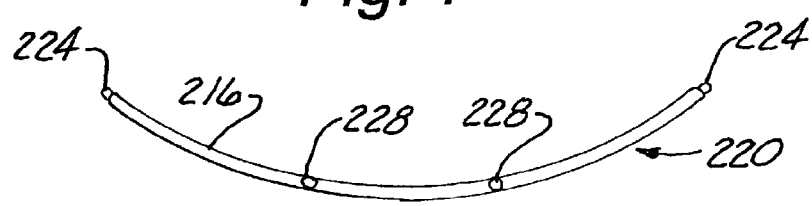
FIG. 8 is a top view of the alternative embodiment of the improved rubber dam frame.
Figure 9:
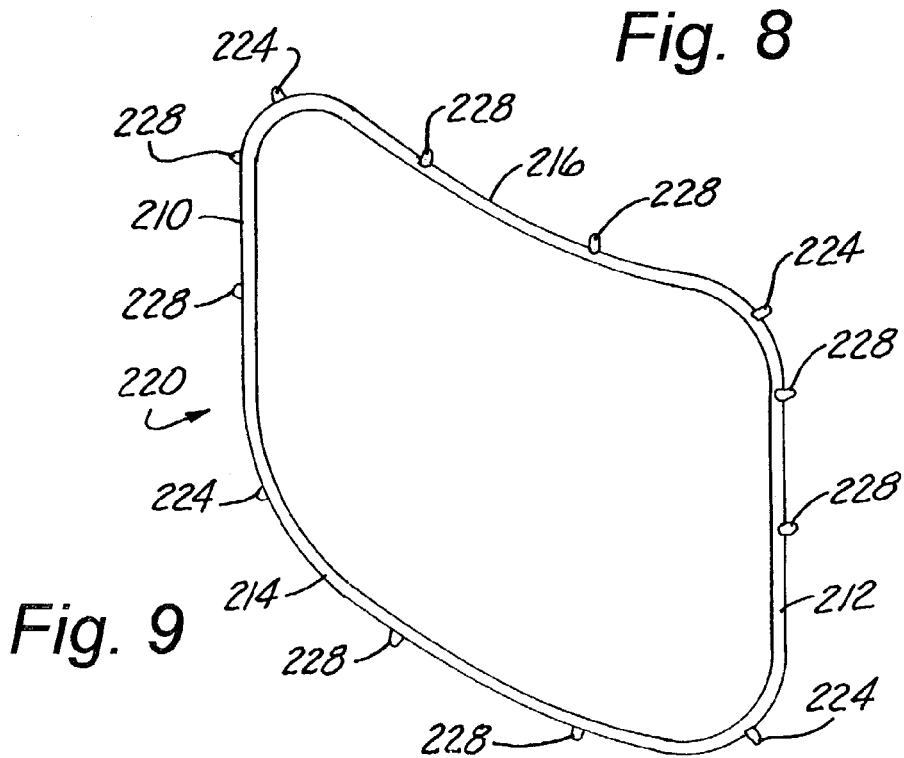
FIG. 9 is an isometric view of the alternative embodiment of the improved rubber dam frame.
Figure 10:
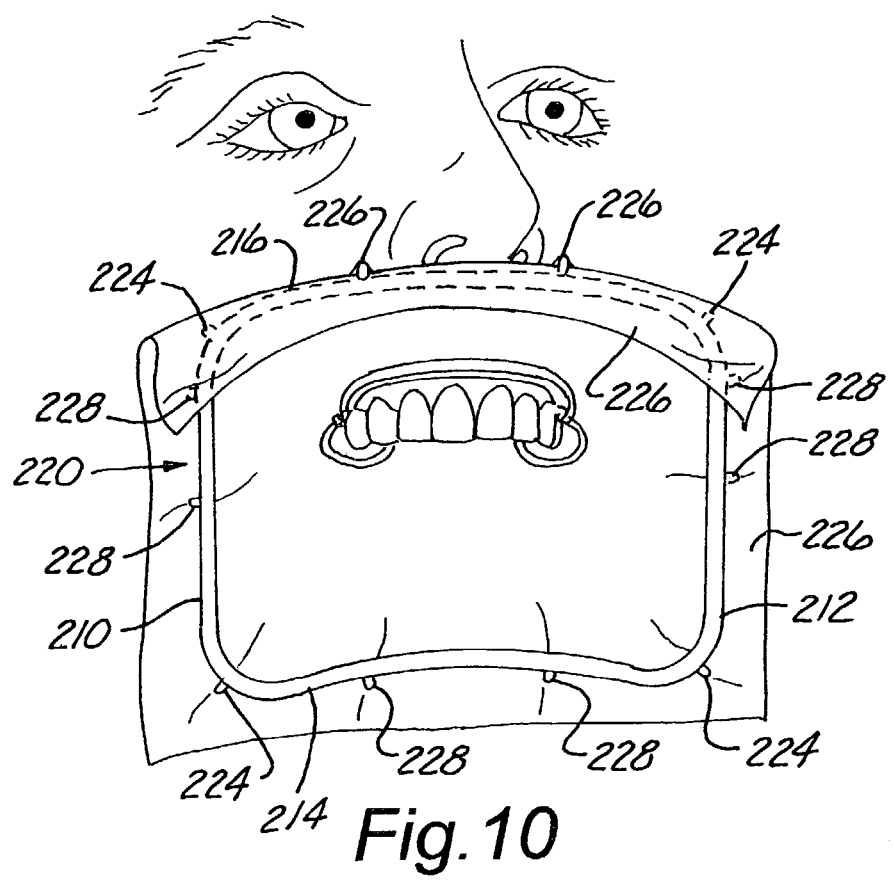
FIG. 10 is an illustration of the alternative embodiment of the improved rubber dam frame as used with the rubber dam membrane.
Figure 11:
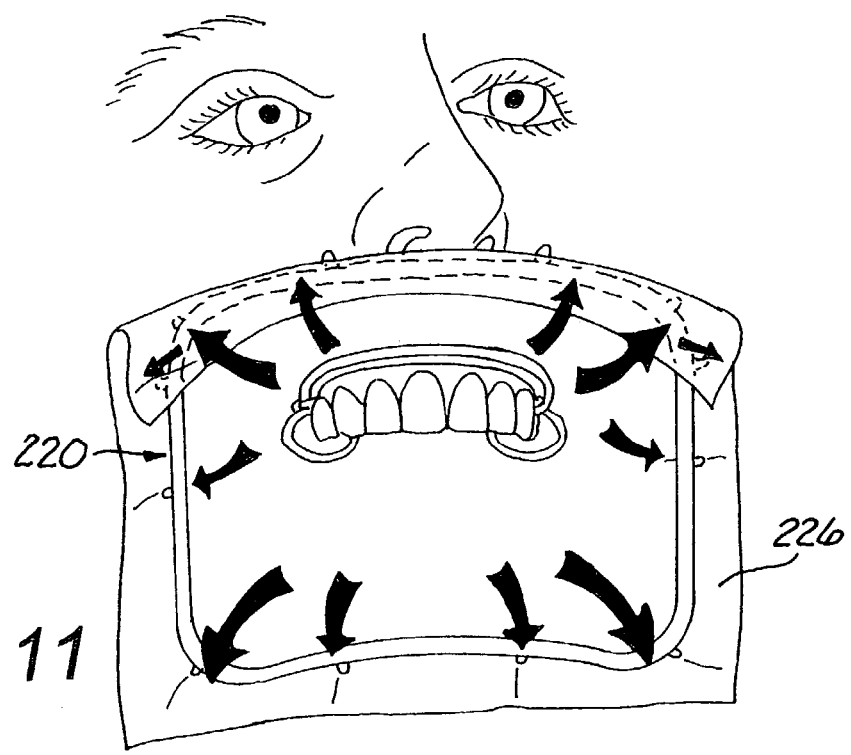
FIG. 11 is an illustration of the alternative embodiment of the improved rubber dam frame as used with the rubber dam membrane stretched over the frame, showing the direction, magnitude, and distribution of vector forces of the stretched rubber dam membrane.
Figure 12:
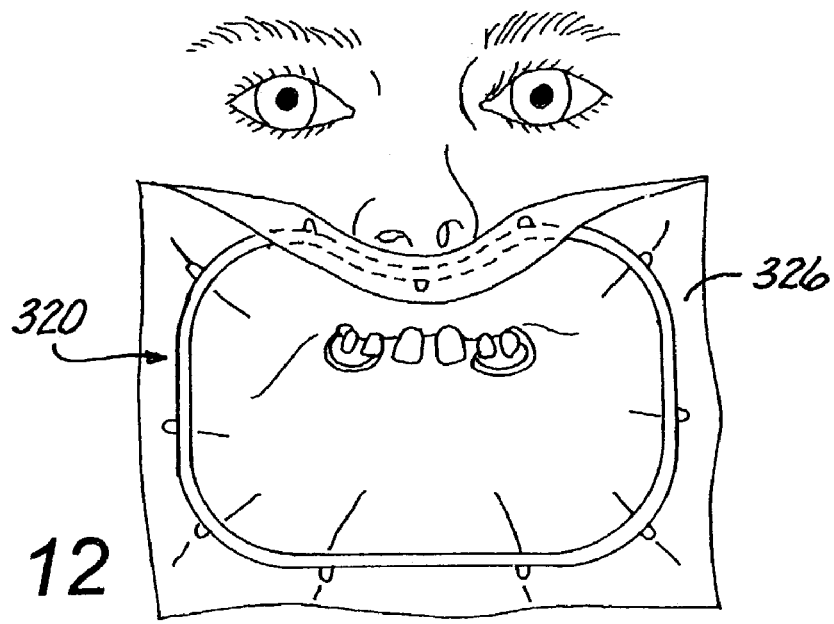
FIG. 12 is an illustration of a pediatric version of the improved rubber dam frame as used with the rubber dam membrane.

FIGS. 7, 8, and 9 illustrate a front view, top view, and isometric view, respectively, of an alternative embodiment of an improved rubber dam frame 220. The major difference of the improved frame 120 from the alternative embodiment frame 220 is the lack of the inwardly facing arc of curvature which circumvents the nose of a patient. As seen in FIG. 7 and FIG. 9, the alternative frame 220 has left and right vertical side elements 210 and 212, a lower horizontal element 214, and an uninterrupted upper horizontal element 216 all joined in a rectilinear manner with rounded corners. The whole frame has an arc of curvature from left to right, as seen in the top view, FIG. 8, which roughly parallels the curvature of the patient's face. Located at each of the four rounded corners are outwardly facing rubber dam corner attachment nibs 224 which attach the rubber dam membrane 226 to the corners of the frame 220. Each of the vertical side elements 210 and 212, has a single outwardly facing side attachment nib 228 which retracts the main body of the rubber dam membrane 226 adjacent to the cheeks of a patient, and each of these vertical side elements 210 and 212 has another outwardly facing side attachment nib 228 for securing excess rubber dam material 226 downward and away from the patient's nose to prevent nasal obstruction. FIG. 10 is an illustration of the alternative embodiment of the improved rubber dam frame 220 with the general field isolation rubber dam 226 stretched over the frame 220 and the excess rubber dam material 226 folded downward and secured against the two vertical side elements 210 and 212 with rubber dam attachment nibs 228. The upper horizontal element 216 has two labial rubber dam side attachment nibs 228 spaced $\frac{1}{3}^{rd}$ of the way across the horizontal element 216. The lower horizontal element 214 also has two labial rubber dam side attachment nibs 228 spaced $\frac{1}{3}^{rd}$ of the way across the lower horizontal element 214. This alternative embodiment of the improved rubber dam frame 220 distributes and balances the internal tensile forces of the stretched rubber dam 226, as illustrated in FIG. 11, in an identical manner to the preferred embodiment, as illustrated in FIG. 6. FIG. 12 illustrates a frame 320 and rubber dam 326 of the present invention in a pediatric version.

Figure 13:
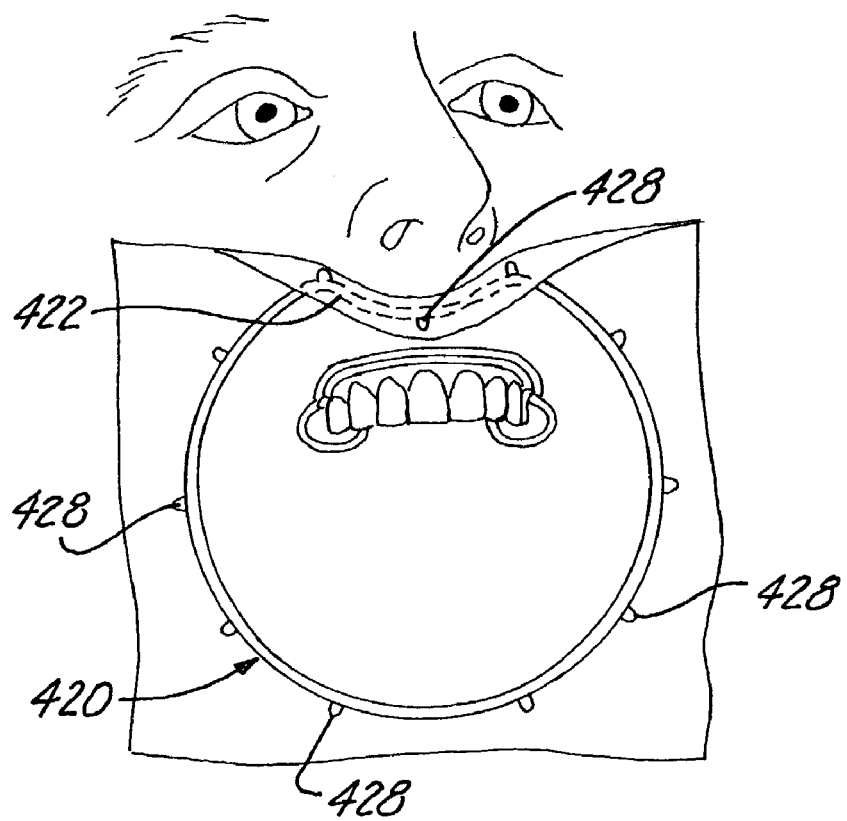
FIG. 13 is an illustration of a circular embodiment of the improved rubber dam frame with an inwardly facing nasal deflection element as used with a rubber dam membrane.

An alternative embodiment, namely a circular frame 420 is illustrated in FIG. 13. The circular frame 420 includes a nasal deflection element 422 located at the top of the circular frame 420. In the preferred embodiment, the nasal deflection element 422 spans approximately 40 degrees, or one-ninth, of the circular frame 420. A plurality of outwardly projected rubber dam attachment nibs 428 are arranged generally symmetrically about the periphery of the circular frame 420 outside of the nasal deflection element 422. A single inwardly projected rubber dam attachment nib 428 is located centrally of the nasal deflection element 422.

With respect to the above-described embodiments, it is to be realized that the general relationships for the parts of the invention are illustrative of the function and manner of operation of said invention, and the assembly and use of said invention should be readily apparent and obvious to one skilled in the art. Equivalent relationships to those illustrated in the drawings and described in the specifications expressing variations in size, materials, shape, form, function, methods, and manner of operation, but which describe equivalent relationships to those illustrated in this disclosure are to be considered to be within the spirit and scope of the invention. Further, since modifications and changes will occur to those skilled in the art, it is not desired to limit the invention to the exact construction and operation shown and described, and accordingly all suitable modifications and equivalents may be resorted to by the inventor as falling within the spirit and scope of the invention. By way of example, although the preferred embodiment presented in this disclosure is of a rectilinear form with rounded corners, an oval, octagonal, or circular design would fall within the spirit and scope of this disclosure, if the frame distributed and increased the vector forces of retraction and stabilization of the rubber dam membrane in the manner equivalent to the way in which the invention prescribes. Another example of equivalency would be the insertion of a semi-circular element which circumvents the nose, as is shown in the preferred embodiment shown in FIGS. 1, 2, and 3. An alternative to a single inwardly facing nib projection is two inwardly facing nibs positioned at junctions of one-thirds of this nasal deflection element. Although the inclusion of this semi-circular element adds to the ability of the frame to reduce interference with the nose, the element is not absolutely necessary. The inclusion of a mechanism to fold excess rubber dam material downward in order to secure it to the frame is not dependent upon the incorporation of the semi-circular element, as is illustrated in the alternative embodiment described and shown in illustration in FIG. 10. This embodiment lacks the semi-circular element, but shows the incorporation of attachment nibs placed on the vertical side elements to triangulate and secure the excess rubber dam material as an alternative. Although attachment nibs may be attached to the side elements as in this fashion, there are other simple mechanisms which could serve just as well, whether located on the side elements or on the upper transverse horizontal element. Two of the three embodiments describe improved rubber dam frames with mechanisms to fold down and restrain the excess rubber dam material, but the second alternative embodiment, an oval framework, may optionally lack an attachment for the excess rubber dam material, or may include this mechanism as disclosed. As long as an embodiment satisfies the design requirements of increasing and distributing the vector forces of the stretched rubber dam in order to provide improved retraction of the patient's lips and soft tissues and to improve stabilization of the rubber dam, while preventing injury to the eyes and face of the patient, the function and manner of operation of the invention is satisfied.

Finally, the material composition of the frame may vary depending on manufacturing requirements, functional criteria, sterilization requirements, and whether the frame is to be reused or is disposable. The preferred material for construction of a noncorrosive, sterilizable, reusable rubber dam frame is stainless steel, although other metals and alloys might be used, along with an exterior plating process to finish the outside of the frame. Alternatively, some plastics and composite materials may also be used for rubber dam frame construction when trying to ease the manufacturing cost, and hence the cost of the product to the end-user. Further, a plastic or composite frame having a pressure sensitive adhesive applied to the frame and covered with a release liner is another alternative means of attaching a rubber dam to a disposable rubber dam frame. The above examples serve to illustrate variations of the embodiment and composition falling within the spirit and scope of the disclosure of the invention, but by no means are an exhaustive discussion of the variation of the invention.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

I claim:

1. A rubber dam frame comprising:
   a. two vertical side leg members;
   b. a single, uninterrupted lower horizontal member;
   c. left and right upper horizontal members;
   d. a downwardly curved concave nasal deflection element, the nasal deflection element positioned between the left and right upper horizontal members;
   e. attachment nibs projected outwardly from the outer perimeter of the frame for attachment of a rubber dam membrane; and
   f. structure for attaching and deflecting excess rubber dam material downward to prevent the material from obstructing the nose and the breathing of the patient.

2. The rubber dam frame as defined in claim 1, wherein the attachment nibs are located at each of four rounded corners of the rubber dam frame.

3. The rubber dam frame as defined in claim 2, further comprising attachment nibs on each of the vertical leg members and the upper and lower horizontal members for evenly distributing vector tensile forces of the stretched elastic rubber dam membrane around the periphery of the rubber dam frame, thereby improving retention and stability of a rubber dam and retraction and support of the patient's lips.

4. The rubber dam frame as defined in claim 1, wherein the structure for deflecting excess rubber dam material from the nose of a patient comprises one or more inwardly facing rubber dam attachment nibs.

5. The rubber dam frame as defined in claim 1, wherein the nasal deflection element is comprised of an upper section of the frame circumventing the patient's nose with an inwardly facing arc of curvature, thereby reducing the interference of the nose and the frame.

6. The rubber dam frame as defined in claim 1, wherein the frame is constructed of stainless steel.

7. The rubber dam frame as defined in claim 1, wherein the frame is comprised of a material selected from the group consisting of rigid, malleable, resilient, and plastic materials.

8. The rubber dam frame as defined in claim 1, wherein the frame is integrally attached to the rubber dam membrane at the time of manufacture.

9. A rubber dam frame as defined in claim 1 used in a dental application to support a rubber dam for isolating a field inside a patient's mouth, wherein the frame supports the rubber dam to deflect the patient's lips and also supports labial bows of the rubber dam.

10. A rubber dam frame as defined in claim 1 used in a dental application to support a rubber dam having a deformable element including labial bows for isolating a field inside a patient's mouth, wherein the frame supports the rubber dam to deflect the patient's lips and also supports the labial bows of the rubber dam.

11. A rubber dam frame comprising:
    a. left and right 180 degree semi-circular side elements;
    b. left and right upper flat transverse horizontal elements;
    c. a downwardly curved semi-circular nasal deflection element;
    d. a lower flat transverse horizontal element;
    e. at least three outwardly facing rubber dam attachment nibs on each of the side semi-circular elements, two positioned at the junction of the semi-circular elements with the flat transverse elements, and one positioned at the midpoint of the semi-circular nasal deflection element;
    f. at least one outwardly facing rubber dam attachment nib on each of the left and right upper flat horizontal elements at their junction with the semi-circular nasal deflection element;
    g. at least two outwardly facing rubber dam attachment nibs on the lower flat transverse horizontal element; and
    h. at least one inwardly facing rubber dam attachment nib on the nasal deflection element.

12. The rubber dam frame as defined in claim 11, wherein the frame is constructed of stainless steel, or other metals or alloys.

13. The rubber dam frame as defined in claim 11, wherein the frame is constructed of plastic or composite materials.

14. The rubber dam frame as defined in claim 11, wherein the frame is comprised of a material selected from the group consisting of rigid, malleable, resilient, and plastic materials.

15. A rubber dam frame comprising:
    a. a circular frame element;
    b. a concave nasal deflection element located symmetrically at the top of the circular frame element;
    c. a plurality of outwardly projected rubber dam attachment nibs located symmetrically about the periphery of the circular frame other than on the nasal deflection element; and
    d. an inwardly projected rubber dam attachment nib located centrally of the concave nasal deflection element.

16. The rubber dam frame as defined in claim 15, wherein the frame is constructed of stainless steel, or other metals or alloys.

17. The rubber dam frame as defined in claim 15, wherein the frame is constructed of plastic or composite materials.

18. The rubber dam frame as defined in claim 15, wherein the frame is comprised of a material selected from the group consisting of rigid, malleable, resilient, and plastic materials.

19. A rubber dam frame comprising:
    a. two vertical side leg members;
    b. a lower horizontal transverse member;
    c. an uninterrupted upper horizontal transverse member;
    d. at least one outwardly directed attachment nib located on each of the vertical side leg members;
    e. at least one outwardly directed attachment nib located on each of the four rounded corners of the frame;
    f. at least two outwardly directed attachment nibs located on the lower horizontal transverse member;
    g. at least two outwardly directed attachment nibs located on the upper horizontal transverse member; and
    h. at least one inwardly directed attachment nib on the upper horizontal transverse member, whereby folding excess rubber dam material onto the at least one inwardly directed attachment nib deflects excess rubber dam material downwardly to prevent obstruction of a patient's nostrils.

20. The rubber dam frame of claim 19 wherein at least one of the members is constructed of malleable material.

21. The rubber dam frame of claim 19 wherein the side leg members and the lower horizontal transverse member and the upper horizontal transverse member together defining a curved surface.

22. A method of preventing obstruction of a patient's nose when using a rubber dam and associated exterior frame, comprising the step of folding down and securing excess rubber dam material to the frame wherein the frame includes a downwardly curved nasal deflection element arid the step of folding down and securing the rubber dam material to the frame comprises deflecting the material in a downwardly concave form which circumvents the patient's nose.

* * * * *